United States Patent

Piccinelli et al.

[11] Patent Number: 5,130,429
[45] Date of Patent: Jul. 14, 1992

[54] PROCESS FOR THE METHYLATION OF TRIAZINE COMPOUNDS CONTAINING 2,2,6,6-TETRAMETHYLPIPERIDINE GROUPS

[75] Inventors: Piero Piccinelli, Bologna; Ivan Orban, Basel; Martin Holer, Magden, both of Switzerland; Valerio Borzatta, Bologna, Italy

[73] Assignee: Ciba-Geigy Corporation, Ardsley, N.Y.

[21] Appl. No.: 800,871

[22] Filed: Nov. 27, 1991

Related U.S. Application Data

[63] Continuation of Ser. No. 586,329, Sep. 18, 1990, abandoned, which is a continuation of Ser. No. 273,783, Nov. 21, 1988, abandoned.

[30] Foreign Application Priority Data

Dec. 4, 1987 [IT] Italy .............................. 228888 A/87

[51] Int. Cl.$^5$ .................... C07D 413/04; C07D 403/04
[52] U.S. Cl. .................... 544/212; 544/113; 544/189; 544/198; 544/209; 540/598
[58] Field of Search ............... 544/113, 189, 209, 212, 544/198; 540/598

[56] References Cited

U.S. PATENT DOCUMENTS

| | | | |
|---|---|---|---|
| 3,898,303 | 8/1975 | Murayama et al. | 544/198 |
| 3,904,581 | 9/1975 | Murayama et al. | 544/198 |
| 3,925,376 | 12/1975 | Chalmers et al. | 544/198 |
| 3,937,711 | 2/1976 | Cook | 544/198 |
| 4,086,204 | 4/1978 | Cassandrini et al. | 544/198 |
| 4,107,139 | 8/1978 | Mayer et al. | 544/198 |
| 4,108,829 | 8/1978 | Cassandrini et al. | 544/198 |
| 4,316,837 | 2/1982 | Molt et al. | 544/198 |
| 4,477,615 | 10/1984 | Raspanti et al. | 544/198 |
| 4,533,688 | 8/1985 | Toda et al. | 544/198 |
| 4,547,548 | 10/1985 | Cantatore | 544/198 |

FOREIGN PATENT DOCUMENTS

| | | | |
|---|---|---|---|
| 0103193 | 3/1984 | European Pat. Off. | 544/198 |
| 0107615 | 5/1984 | European Pat. Off. | 544/198 |
| 2194237 | 3/1988 | United Kingdom | 544/198 |

Primary Examiner—Johann Richter
Attorney, Agent, or Firm—Luther A. R. Hall

[57] ABSTRACT

Process for the methylation of compounds at least one group of the formula (I)

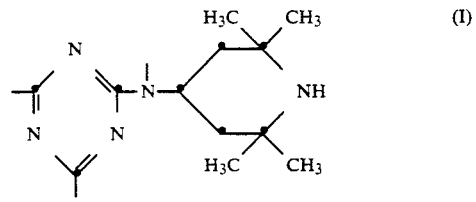

by means of a mixture of formaldehyde and formic acid in a reaction medium consisting of an aromatic hydrocarbon solvent.

15 Claims, No Drawings

PROCESS FOR THE METHYLATION OF TRIAZINE COMPOUNDS CONTAINING 2,2,6,6-TETRAMETHYLPIPERIDINE GROUPS

This application is a continuation of application Ser. No. 586,329, filed Sep. 18, 1990, now abandoned which is a continuation of Ser. No. 273,783 filed Nov. 21, 1988, now abandoned.

The present invention relates to a novel process for the preparation of triazine compounds containing 1,2,2,6,6-pentamethylpiperidine groups.

In particular, the present invention relates to a simple and convenient process for the preparation of 1,2,2,6,6-pentamethyl-4-piperidylaminotriazine compounds containing one or more triazine rings, which process is based on the methylation of the corresponding 2,2,6,6-tetramethylpiperidine derivatives by means of formaldehyde and formic acid and which is operated in an aromatic hydrocarbon solvent.

Triazine derivatives of 2,2,6,6-tetramethyl-4-piperidylamine can be used as light stabilizers and heat stabilizers for synthetic polymers, as reported, for example, in U.S. Pat. Nos. 4,086,204 and 4,108,829 and EP-A-107,615.

Moreover, it was shown in GB-A-2,194,237 that certain triazine derivatives of 1,2,2,6,6-pentamethyl-4-piperidylamine also have remarkable antioxidant properties in the case of polyolefines.

Considerable interest has therefore arisen in an economical and industrially applicable process for the methylation of triazine derivatives of 2,2,6,6-tetramethyl-4-piperidylamine. It is known that numerous derivatives of 2,2,6,6-tetramethylpiperidine can be obtained starting from triacetoneamine (2,2,6,6-tetramethyl-4-piperidone).

The methylation of these piperidine compounds in the 1-position has hitherto been carried out in various ways, the methylating agents used being methyl iodide, methyl sulfate, methyl p-toluenesulfonate, formaldehyde and formic acid (Eschweiler-Clarke reaction) or formaldehyde, hydrogen and a hydrogenation catalyst (reductive methylation).

This last process is very advantageous for the methylation of simple derivatives of 2,2,6,6-tetramethylpiperidine, for example 2,2,6,6-tetramethyl-4-piperidinol, but it is not suitable for the preparation of more complex compounds. In this case, the only process feasible in practice is that based on the Eschweiler-Clarke reaction; this has in fact frequently been used for the preparation of various 1,2,2,6,6-pentamethylpiperidine compounds, as reported, for example, in U.S. Pat. Nos. 3,898,303, 3,904,581, 3,937,711, 4,107,139, 4,316,837 and 4,533,688 and in EP-A-103,193.

The above mentioned process, which can be schematically represented by the reaction

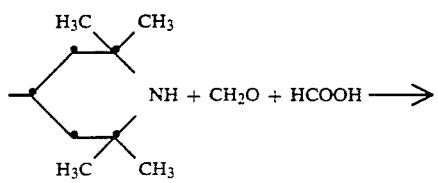

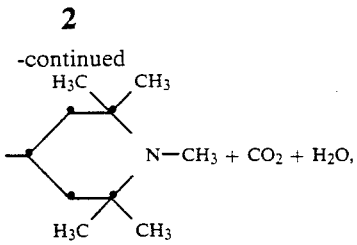

consists in heating the 2,2,6,6-tetramethylpiperidine, already isolated from the reaction mixture, for several hours with an excess of aqueous formaldehyde and formic acid, rendering the mixture alkaline to a pH>9 at the end of the reaction and then, by filtration, separating off the methylated product which, after repeated washing to remove the excess alkali, is finally dried. The process is long and costly and, therefore, a need is felt for providing a simpler and more economical process which can be used on an industrial scale.

A very advantageous methylation process has now been found, which is particularly suitable for the preparation of 1,2,2,6,6-pentamethyl-4-piperidylaminotriazine compounds.

Compared with the known state of the art, the process according to the present invention has various advantages which can be summarized as follows:

a) direct use of the reaction mixture obtained from cyanuric chloride and 2,2,6,6-tetramethyl-4-piperidylamine in an aromatic hydrocarbon solvent containing the tetramethylpiperidine derivative, without isolation of the latter;

b) use of a smaller excess of formaldehyde and formic acid;

c) shortened reaction times;

d) almost complete elimination of the $CO_2$ produced in the reaction;

e) considerable reduction in the quantity of aqueous reflux; in fact, the use of a smaller excess of formic acid and the almost complete elimination of $CO_2$ from the reaction mixture permit a significant reduction in the quantity of inorganic base required to neutralize the methylated product, so that the quantity of by-products to be eliminated is reduced;

f) higher purity of the product obtained, since complete methylation of the >NH groups in the piperidine is assured; this corresponds to a higher yield of methylated product.

The significant reduction in the working times, the use of smaller quantities of reagents and the higher yields make the process according to the present invention very attractive economically and hence suitable for use on an industrial scale.

The present invention relates to a process for the methylation of compounds containing at least one group of the formula (I)

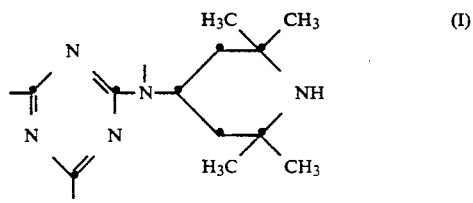

by means of a mixture of formaldehyde and formic acid to give the corresponding compound containing at least one group of the formula (II)

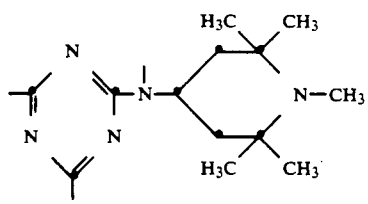
(II)

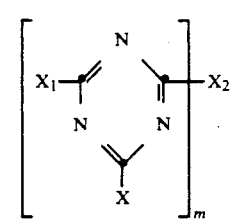
(III)

which comprises effecting the said methylation in an aromatic hydrocarbon solvent. Preferably, the water of reaction and that contained in the reagents is simultaneously separated off by azeotropic distillation.

In the process according to the present invention, the formaldehyde is preferably used as a 30–50% (weight/volume) aqueous solution and the formic acid can contain up to 30% (weight/volume) of water.

The aromatic hydrocarbon solvent used is, for example, toluene, xylene or trimethylbenze and preferably xylene.

Those procedures are of particular interest in which the molar ratio of the >NH groups in the piperidine of the formula (I), formaldehyde and formic acid is 1:1:1 to 1:2:2, preferably 1:1:1 to 1:1.3:1.3 and in particular 1:1:1 to 1:1.2:1.2.

The reaction temperature is 80° to 150° C., preferably 90° to 130° C.

When the reaction has ended, the unreacted formic acid and the residual $CO_2$ are e.g. neutralized with an aqueous solution of an inorganic base, preferably sodium hydroxide or potassium hydroxide. After the aqueous phase (containing the unreacted formaldehyde beside formate and carbonate) has been separated off, the organic phase is washed with water until neutral. The water which has remained in the organic phase is conveniently removed azeotropically and the solvent is evaporated to give the methylated product.

The methylated product thus obtained can be used directly or, if desired, can be purified by usual methods, for example by crystallization.

The formaldehyde for the methylation reaction is preferably free of methanol; this can be obtained from paraformaldehyde, for example by dissolving the latter in water in the presence of about 2–3% of sodium hydroxide. It is also possible directly to use paraformaldehyde suspended in water in a quantity necessary to obtain a $CH_2O$ concentration equal to 30–50%.

If >NH groups bound directly to the triazine ring are also present in the compounds containing groups of the formula (I), a total or partial methylation of these groups may be possible, the extent of this methylation depending on the quantity of the reagents used and on the reaction temperature; higher temperatures favour this methylation.

The compounds containing one or more groups of the formula (I) can be prepared by known methods, for example by reacting cyanuric chloride with 2,2,6,6-tetramethyl-4-piperidylamine, as described, for example, in U.S. Pat. Nos. 3,925,376, 4,086,204, 4,108,829, 4,477,615 and 4,547,548.

In particular, compounds which contain groups of the formula (II) and which can be prepared by the present invention are:

1) Compounds of the formula (III)

in which X and $X_1$, which can be identical or different, are one of the groups

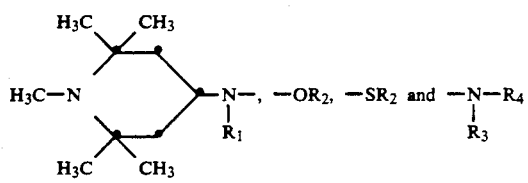

where $R_1$ is hydrogen, $C_1-C_{12}$alkyl, $C_5-C_7$cycloalkyl which is unsubstituted or substituted by $C_1-C_4$alkyl, $C_2-C_4$alkyl monosubstituted in the 2-, 3- or 4-position by OH, $C_1-C_8$alkoxy or $C_2-C_8$dialkylamino, benzyl or 1,2,2,6,6-pentamethyl-4-piperidyl, $R_2$ is $C_1-C_{12}$alkyl, $C_5-C_7$cycloalkyl which is unsubstituted or substituted by $C_1-C_4$alkyl, allyl, phenyl, benzyl or 1,2,2,6,6-pentamethyl-4-piperidyl and $R_3$ and $R_4$, which can be identical or different, are hydrogen, $C_1-C_{12}$alkyl, $C_5-C_7$cycloalkyl which is unsubstituted or substituted by $C_1-C_4$alkyl, allyl, $C_2-C_4$alkyl mono-substituted in the 2-, 3- or 4-position by OH, $C_1-C_8$alkoxy or $C_2-C_8$dialkylamino, or benzyl, or $R_3$ and $R_4$, together with the nitrogen atom to which they are linked, form part of a 5-membered to 7-membered heterocyclic ring, m is an integer from 1 to 6 and, if m is 1, $X_2$ is as defined above for X and $X_1$ or is Cl or Br and, if m is 2, $X_2$ is one of the groups of the formulae (IV)–(IVe)

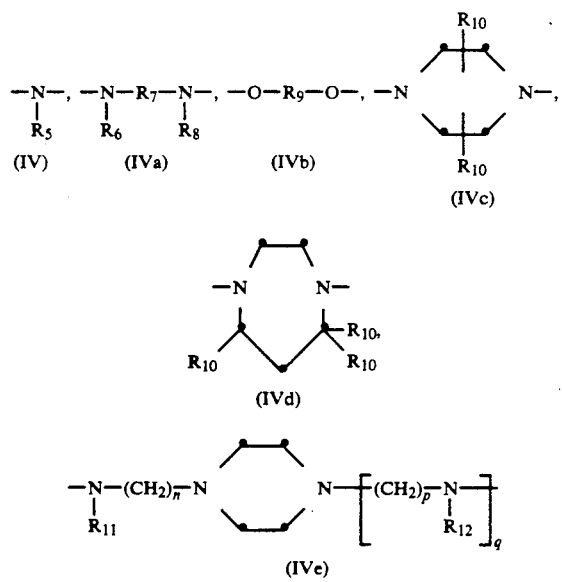

in which $R_5$ is as defined above for $R_1$, and $R_6$, $R_8$, $R_{11}$ and $R_{12}$, which can be identical or different, are hydrogen, $C_1-C_{12}$alkyl, $C_5-C_7$cycloalkyl which is unsubstituted or substituted by $C_1-C_4$alkyl or are benzyl or 1,2,2,6,6-pentamethyl-4-piperidyl, $R_7$ is $C_2$-$C_{12}$alkylene, $C_5$-$C_{18}$cycloalkylene, $C_8$-$C_{18}$dialkylenecyclohexylene, $C_{13}$-$C_{18}$alkylenedicyclohexylene, $C_{14}$-$C_{18}$alkylidenedicyclohexylene, xylylene, $C_4$-$C_{12}$alkylene which is interrupted by one, two or three oxygen atoms or $>N\!-\!R_{13}$ groups, $R_{13}$ being $C_1$-$C_{12}$alkyl or cyclohexyl, $R_9$ is $C_2$-$C_{12}$alkylene, $C_5$-$C_{18}$cycloalkylene, $C_8$-$C_{18}$dialkylenecyclohexylene, $C_{13}$-$C_{18}$alkylenedicyclohexylene, $C_{14}$-$C_{18}$alkylidenedicyclohexylene, phenylene, $C_{13}$-$C_{26}$alkylenediphenylene or $C_{14}$-$C_{26}$alkylidenediphenylene which is unsubstituted or substituted on the benzene ring by $C_1$-$C_4$alkyl, $R_{10}$ is hydrogen or methyl, n and p, which can be identical or different, are integers from 2 to 6 and q is zero or 1, and, if m is 3, $X_2$ is one of the groups

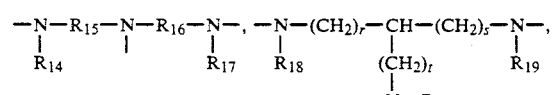

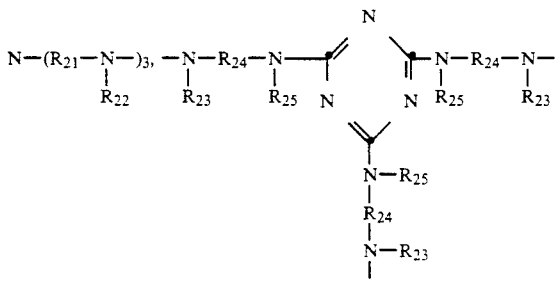

in which $R_{14}$, $R_{17}$, $R_{18}$, $R_{19}$, $R_{20}$, $R_{22}$, $R_{23}$ and $R_{25}$, which can be identical or different, are as defined for $R_6$ and $R_8$, and $R_{15}$, $R_{16}$, $R_{21}$ and $R_{24}$, which can be identical or different, are $C_2$-$C_{12}$alkylene, or $R_{15}$ and $R_{16}$ are $C_4$-$C_6$alkylene which is interrupted by an $>N\!-\!CH_3$ group, r and s, which can be identical or different, are integers from 2 to 6 and t is zero or 1, and, if m is 4, 5 or 6, $X_2$ is a group

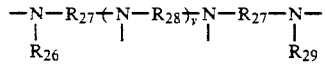

where $R_{26}$ and $R_{29}$, which can be identical or different, are as defined for $R_6$ and $R_8$, and $R_{27}$ and $R_{28}$, which can be identical or different, are $C_2$-$C_{12}$alkylene and v is 1, 2 or 3, or, if m is 4, $X_2$ is additionally one of the groups

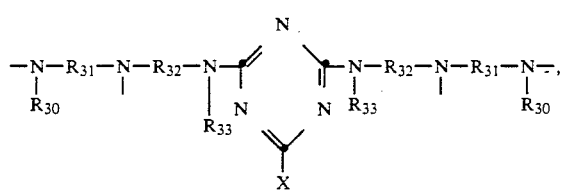

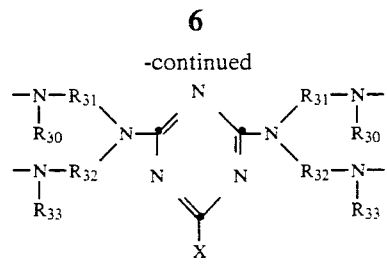

where $R_{30}$ and $R_{33}$, which can be identical or different, are as defined above for $R_6$ and $R_8$, and $R_{31}$ and $R_{32}$, which can be identical or different, are $C_2$-$C_{12}$alkylene and X is as defined above, or, if m is 6, $X_2$ is additionally one of the groups

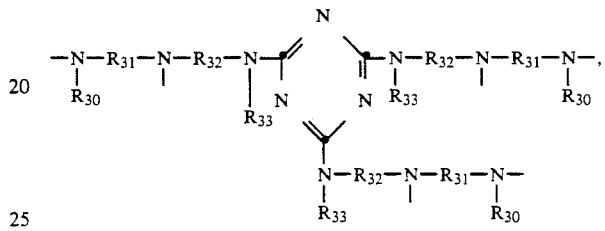

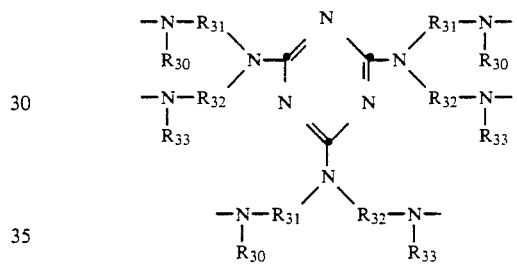

where $R_{30}$, $R_{31}$, $R_{32}$ and $R_{33}$ are as defined above, with the proviso that, in these compounds of the formula (III), at least one 1,2,2,6,6-pentamethyl-4-piperidyl group is present in at least one of the groups X, $X_1$ and $X_2$.

2) Compound of the formula (V)

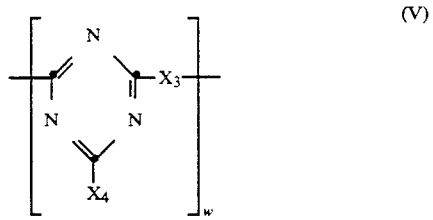

in which $X_3$ is one of the groups of the above formulae (IVa), (IVb), (IVc), (IVd) and (IVe) or a group of the formula

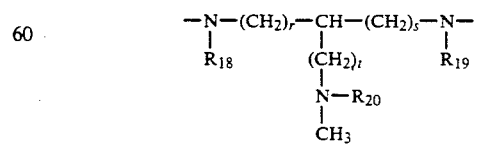

in which $R_{18}$, $R_{19}$, $R_{20}$, r, s and t are as defined above, $X_4$ is as defined above for the groups X and $X_1$, and w is a number from 2 to 50, the first end group attached to the triazine group being, for example, Cl, ONa, OK, a group $X_4$ or one of the groups

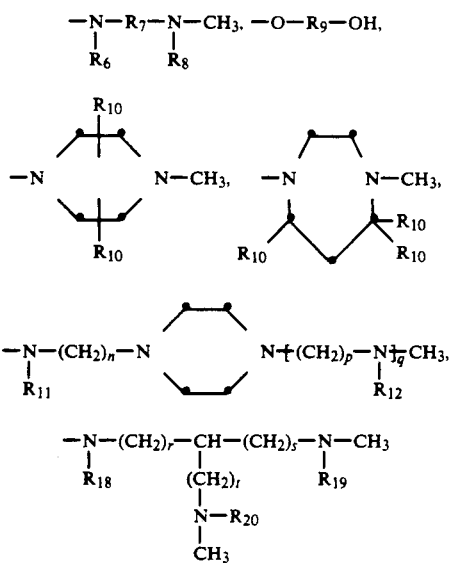

in which $R_6$, $R_7$, $R_8$, $R_9$, $R_{10}$, $R_{11}$, $R_{12}$, $R_{18}$, $R_{19}$, $R_{20}$, n, p, q, r, s and t are as defined above, the second end group attached to the radical $X_3$ being, for example, methyl, OH or a group

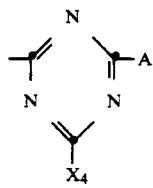

where A has one of the definitions given above for the first end group and $X_4$ is as defined above, with the proviso that, in these compounds of the formula (V) at least one 1,2,2,6,6-pentamethyl-4-piperidyl group is present in at least one of the groups $X_3$ and $X_4$.

3) Polytriazines containing recurring units of the formulae (VI) and (VII)

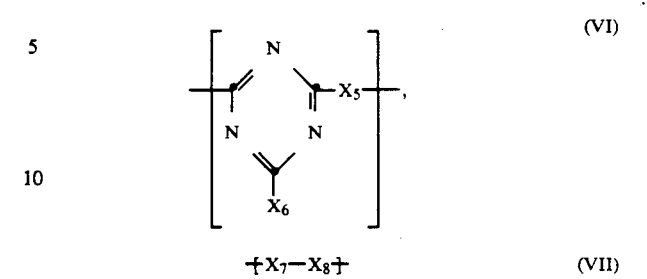

and having a molecular weight between 1000 and 20,000, in which the (VI):(VII) molar ratio is 4:1 to 1:4, $X_5$ and $X_8$, which can be identical or different, are as defined above for $X_3$, $X_6$ is as defined above for X and $X_1$, $X_7$ is $C_2$-$C_{12}$alkylene, a group $$-CH_2CHCH_2-,$$
$$\phantom{-CH_2C}OH$$

aliphatic $C_2$-$C_{12}$-diacyl, —$CH_2CO$—, a group —COO—$R_9$—OOC— with $R_9$ as defined above, or $X_7$ is a group

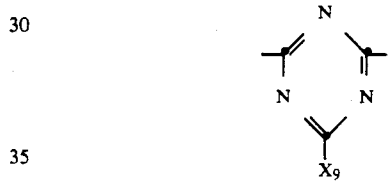

with $X_9$ as defined above for X and $X_1$, with the proviso that, in these compounds, at least one 1,2,2,6,6-pentamethyl-4-piperidyl group is present in at least one of the radicals $X_5$, $X_6$ and $X_8$.

4) Compounds of the formula (VIII)

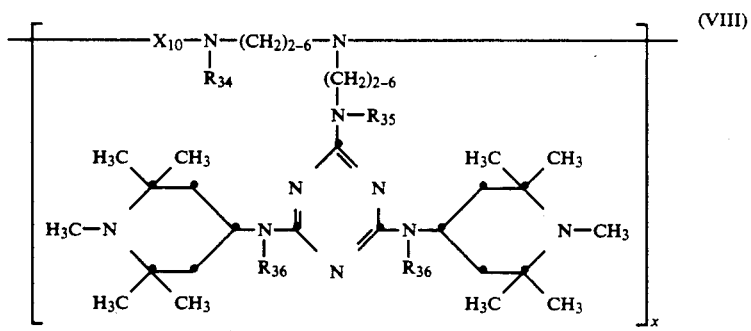

where $X_{10}$ is as defined above for $X_7$, $R_{34}$ and $R_{35}$, which can be identical or different, are hydrogen or $C_1$-$C_{12}$alkyl or $R_{34}$ is additionally a group of the formula (IX)

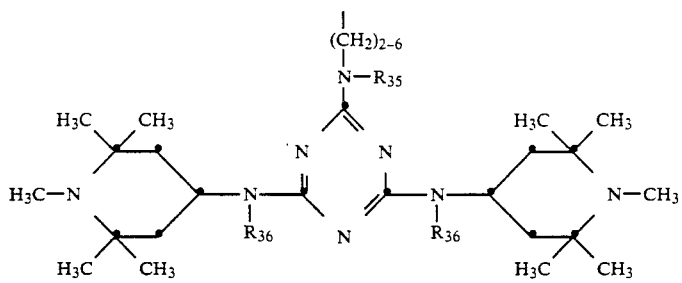

(IX)

with $R_{35}$ as defined above, $R_{36}$ is hydrogen, $C_1$–$C_{12}$alkyl, cyclohexyl or benzyl, and x is a number from 2 to 50.

The various $C_1$–$C_{12}$alkyl substituents are linear or branched and are, for example, methyl, ethyl, propyl, isopropyl, butyl, 2-butyl, iso-butyl, t-butyl, pentyl, hexyl, heptyl, octyl, 2-ethylhexyl, nonyl, decyl, undecyl or dodecyl.

The various $C_5$–$C_7$cycloalkyl substituents, which are unsubstituted or substituted by $C_1$–$C_4$alkyl, in particular methyl, are, for example, cyclopentyl, cyclohexyl, methylcyclohexyl, dimethylcyclohexyl, trimethylcyclohexyl and preferably cyclohexyl.

Examples of $C_2$–$C_4$alkyl monosubstituted in the 2-, 3- or 4-position by OH are 2-hydroxyethyl, 2-hydroxypropyl, 3-hydroxypropyl, 2-hydroxybutyl and 4-hydroxybutyl.

Examples of $C_2$–$C_4$alkyl monosubstituted in the 2-, 3- or 4-position by $C_1$–$C_8$alkoxy are 2-methoxyethyl, 2-ethoxyethyl, 2-butoxyethyl, 3-methoxypropyl, 3-ethoxypropyl, 3-butoxypropyl, 3-octoxypropyl and 4-methoxybutyl.

Examples of $C_2$–$C_4$alkyl monosubstituted in the 2-, 3- or 4-position by $C_2$–$C_8$dialkylamino are 2-diethylaminoethyl, 2-dibutylaminoethyl, 3-dimethylaminopropyl, 3-diethylaminopropyl and 3-dibutylaminopropyl.

Representative examples of $R_3$ and $R_4$ which, together with the nitrogen atom to which they are linked, form part of a 5-membered to 7-membered heterocyclic ring, which can contain a further heteroatom such as oxygen or nitrogen, are 1-pyrrolidinyl, 1-piperidinyl, 4-morpholinyl, 4-methyl-1-piperazyl and 1-hexahydroazepinyl.

Examples of $C_2$–$C_{12}$alkylene are ethylene, propylene, trimethylene, tetramethylene, pentamethylene, 2,2-dimethyltrimethylene, hexamethylene, heptamethylene, octamethylene, trimethylhexamethylene, decamethylene, undecamethylene and dodecamethylene.

Examples of $C_5$–$C_{18}$cycloalkylene are cyclohexylene or cyclohexylene substituted by $C_1$–$C_4$alkyl.

Examples of $C_8$–$C_{18}$dialkylenecycloalkylene are cyclohexylenedimethylene and dimethylcyclohexylenedimethylene.

Examples of $C_{13}$–$C_{18}$alkylidenedicyclohexylene are methylenedicyclohexylene and methylene-bis-(dimethylcyclohexylene).

An example of $C_{14}$–$C_{18}$alkylidenedicyclohexylene is isopropylidenedicyclohexylene.

Examples of $C_4$–$C_{12}$alkylene interrupted by 1, 2 or 3 oxygen atoms are 3-oxapentane-1,5-diyl, 4-oxaheptane-1,7-diyl, 3,6-dioxaoctane-1,8-diyl-4,9-dioxadodecane-1,12-diyl, 3,6,9-trioxaundecane-1,11-diyl and 4,7,10-trioxatridecane-1,13-diyl.

Representative examples of $C_4$–$C_{12}$alkylene $R_7$ interrupted by one, two or three >N—$R_{13}$ groups are 3-methyl-3-azapentane-1,5-diyl, 4-methyl-4-azaheptane-1,7-diyl, 4-butyl-4-azaheptane-1,7-diyl, 4-octyl-4-azaheptane-1,7-diyl, 4-cyclohexyl-4-azaheptane-1,7-diyl, 7-methyl-7-azatridecane-1,13-diyl, 4,7-dimethyl-4,7-diazadecane-1,10-diyl and 3,6,9-triazaundecane-1,11-diyl.

Representative examples of $C_{13}$–$C_{26}$alkylenediphenylene or $C_{14}$–$C_{26}$alkylidenediphenylene $R_9$, which is unsubstituted or substituted on the benzene ring by $C_1$–$C_4$alkyl, are methylenediphenylene, isopropylidenediphenylene, butylidenediphenylene or a group of the formula

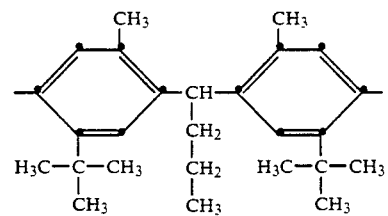

Preferred examples of $C_4$–$C_6$alkylene $R_{15}$ and $R_{16}$ interrupted by an >N—$CH_3$ group are 3-methyl-3-azapentane-1,5-diyl, 3-methyl-3-azahexane-1,6-diyl and 4-methyl-4-azaheptane-1,7-diyl.

Aliphatic $C_2$–$C_{12}$diacyl $X_7$ and $X_{10}$ are preferably $C_2$–$C_{10}$alkanedioyl, in particular oxalyl, malonyl, succinyl, adipoyl or sebacoyl.

The preferred compounds of the formula (III) are those of the formula (IIIa)

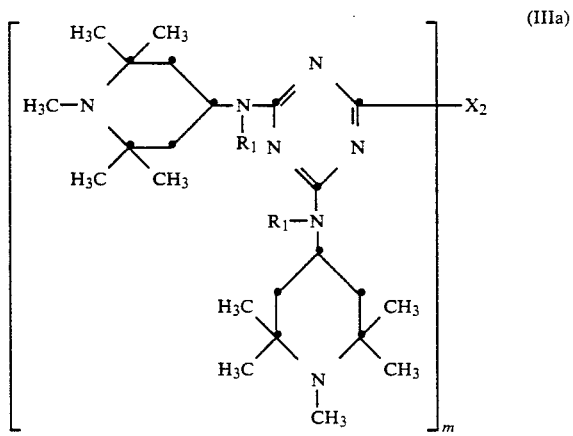

(IIIa)

in which $R_1$ is $C_1$–$C_8$alkyl, cyclohexyl, 1,2,2,6,6-pentamethyl-4-piperidyl or $C_2$–$C_3$alkyl monosubstituted in the 2- or 3-position by OH, $C_1$–$C_4$alkoxy or $C_2$–$C_4$dialkylamino, m is an integer from 1 to 4, and, if m is 1, X₂ is Cl or one of the groups

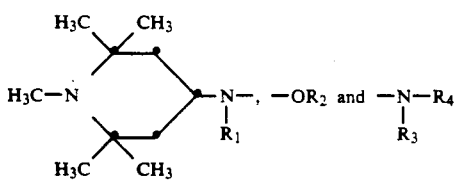

where R₁ is as defined above, R₂ is $C_1$-$C_8$alkyl or 1,2,2,6,6-pentamethyl-4-piperidyl and R₃ and R₄, which can be identical or different, are hydrogen, $C_1$-$C_8$alkyl, cyclohexyl or allyl or

represents 4-morpholinyl, and, if m is 2, X₂ is one of the groups

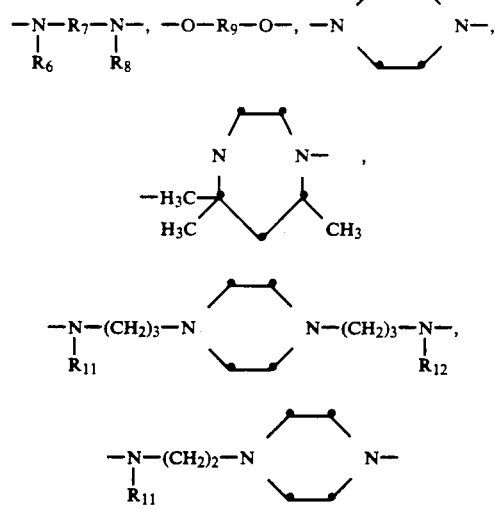

where R₆, R₈, R₁₁ and R₁₂, which can be identical or different, are hydrogen, $C_1$-$C_4$alkyl, cyclohexyl or 1,2,2,6,6-pentamethyl-4-piperidyl, R₇ is $C_2$-$C_6$alkylene, cyclohexylene, cyclohexylenedimethylene, methylenedicyclohexylene or $C_4$-$C_{12}$alkylene which is interrupted by one or two oxygen atoms or >N—CH₃ groups and R₉ is $C_2$-$C_6$alkylene, cyclohexylene, cyclohexylenedimethylene, isopropylidenedicyclohexylene, phenylene, methylenediphenylene or isopropylidenediphenylene, and, if m is 3, X₂ is a group

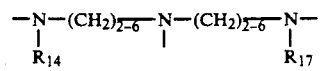

where R₁₄ and R₁₇, which can be identical or different, are hydrogen, $C_1$-$C_4$alkyl or 1,2,2,6,6-pentamethyl-4-piperidyl, and, if m is 4, X₂ is a group

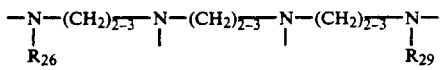

where R₂₆ and R₂₉, which can be identical or different, are hydrogen, $C_1$-$C_4$alkyl or 1,2,2,6,6-pentamethyl-4-piperidyl.

If m is 2, other preferred compounds of the formula (III) are those of the formula

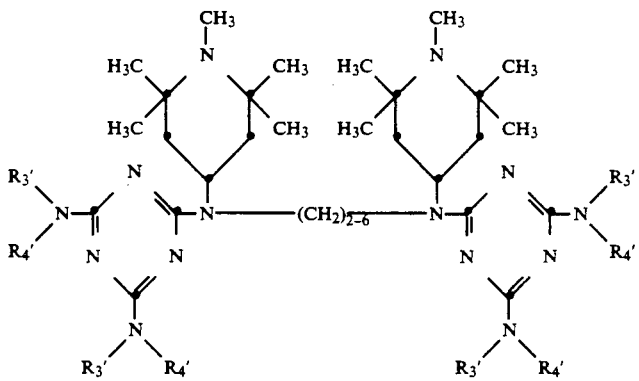

in which R₃' and R₄' are $C_1$-$C_4$alkyl or allyl and R₃' is additionally hydrogen, or the group

is 4-morpholinyl.

Preferred compounds of the formula (V) are those of the formula (Va)

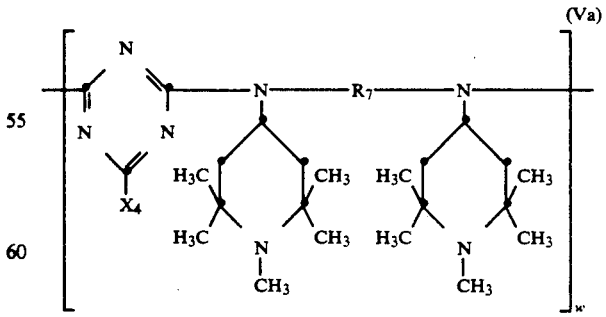

in which R₇ is $C_2$-$C_6$alkylene, cyclohexylene, cyclohexylenedimethylene, methylenedicyclohexylene or $C_4$-$C_{12}$alkylene which is interrupted by one or two oxygen atoms or >N—CH₃ groups, X₄ is one of the groups

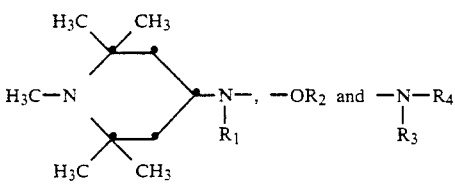

where $R_1$ is $C_1$-$C_8$alkyl, cyclohexyl, 1,2,2,6,6-pentamethyl-4-piperidyl or $C_2$-$C_3$alkyl monosubstituted in the 2- or 3-position by OH, $C_1$-$C_4$alkoxy or $C_2$-$C_4$dialkylamino, $R_2$ is $C_1$-$C_8$alkyl or 1,2,2,6,6-pentamethyl-4-piperidyl, $R_3$ and $R_4$, which can be identical or different, are hydrogen, $C_1$-$C_8$alkyl, cyclohexyl or allyl, or

is 4-morpholinyl, w is a number from 2 to 20, the first end group bound to the triazine radical being, for example, ONa, OK or a group $X_4$ and the second end group bound to the nitrogen atom in the chain being, for example, methyl or a group

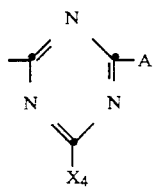

where A is, for example, ONa, OK or the group $X_4$ and $X_4$ is as defined above.

Preferred polytriazines containing recurring units of the formulae (VI) and (VII) are those having a molecular weight between 1500 and 10,000 and a (VI):(VII) molar ratio of 3:1 to 1:3, in which $X_5$ and $X_8$ are groups of the formula

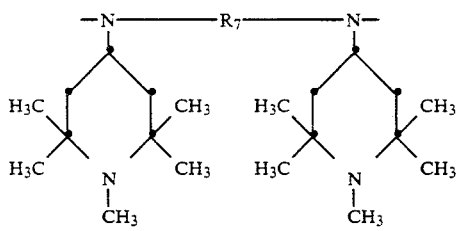

where $R_7$ is $C_2$-$C_6$alkylene, cyclohexylene, cyclohexylenedimethylene, methylenedicyclohexylene or $C_4$-$C_{12}$alkylene which is interrupted by one or two oxygen atoms or $>N$—$CH_3$ groups, $X_6$ is one of the groups

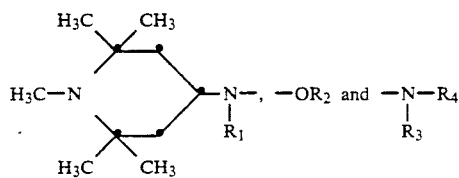

where $R_1$ is $C_1$-$C_8$alkyl, cyclohexyl, 1,2,2,6,6-pentamethyl-4-piperidyl or $C_2$-$C_3$alkyl monosubstituted in the 2- or 3-position by OH, $C_1$-$C_4$alkoxy or $C_2$-$C_4$dialkylamino, $R_2$ is $C_1$-$C_8$alkyl or 1,2,2,6,6-pentamethyl-4-piperidyl and $R_3$ and $R_4$, which can be identical or different, are hydrogen, $C_1$-$C_8$alkyl, cyclohexyl or allyl, or

is 4-morpholinyl and $X_7$ is

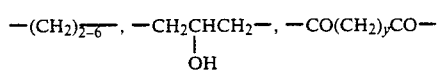

with y being zero to 8, or —$CH_2CO$—.

Those compounds of the formula (VIII) are preferred in which $X_{10}$ is

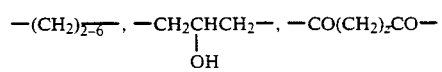

with z being zero to 8, a —$CH_2CO$— group or a group

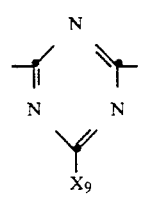

where $X_9$ is one of the groups

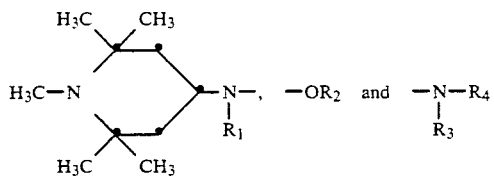

in which $R_1$ is $C_1$-$C_8$alkyl, cyclohexyl or 1,2,2,6,6-pentamethyl-4-piperidyl, $R_2$ is $C_1$-$C_8$alkyl or 1,2,2,6,6-pentamethyl-4-piperidyl, and $R_3$ and $R_4$, which can be identical or different, are hydrogen, $C_1$-$C_8$alkyl, cyclohexyl or allyl, or

is 4-morpholinyl, $R_{34}$ and $R_{35}$, which can be identical or different, are hydrogen or methyl, or $R_{34}$ is a group of the formula (IX) with $R_{35}$ being hydrogen or methyl, $R_{36}$ is $C_1$-$C_8$alkyl or cyclohexyl and x is a number from 2 to 20.

Particularly preferred compounds which contain groups of the formula (II) and which can be prepared in accordance with the present invention are:

a) the compounds of the formula (IIIa) in which $R_1$ is $C_1$-$C_8$alkyl, cyclohexyl or 1,2,2,6,6-pentamethyl-4-piperidyl, m is an integer from 1 to 4, and, if m is 1, $X_2$ is Cl or one of the groups

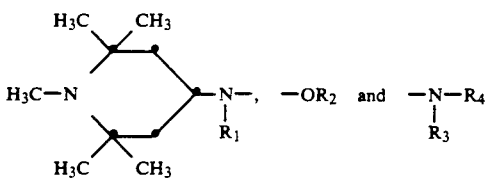

where $R_1$ is as defined above, $R_2$ is $C_1$–$C_8$alkyl or 1,2,2,6,6-pentamethyl-4-piperidyl, and $R_3$ and $R_4$, which can be identical or different, are $C_1$–$C_8$alkyl, cyclohexyl or allyl, and $R_3$ can also be hydrogen, or

is 4-morpholinyl, and, if m is 2, $X_2$ is one of the groups

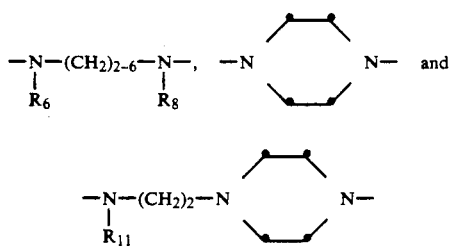

where $R_6$, $R_8$ and $R_{11}$, which can be identical or different, are hydrogen, methyl or 1,2,2,6,6-pentamethyl-4-piperidyl, and, if m is 3, $X_2$ is a group

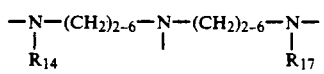

where $R_{14}$ and $R_{17}$, which can be identical or different, are hydrogen, methyl or 1,2,2,6,6-pentamethyl-4-piperidyl, and, if m is 4, $X_2$ is a group

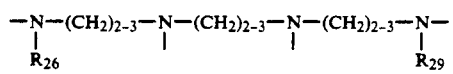

where $R_{26}$ and $R_{29}$, which can be identical or different, are hydrogen or methyl; and b) the compounds of the formula (Va) in which $R_7$ is —$(CH_2)_{2-6}$—, $X_4$ is one of the groups

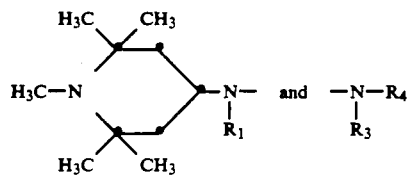

where $R_1$ is $C_1$–$C_8$alkyl, cyclohexyl or 1,2,2,6,6-pentamethyl-4-piperidyl, $R_3$ and $R_4$, which can be identical or different, are $C_1$–$C_8$alkyl or cyclohexyl, and $R_3$ can also be hydrogen, or

is 4-morpholinyl, w is a number from 2 to 10, and the end group bound to the triazine radical is, for example, one of the groups $X_4$ as defined above and the end group bound to the nitrogen atom in the chain is, for example, methyl or a group

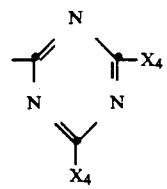

with $X_4$ being as defined above.

The process according to the instant invention is especially useful for the preparation of the compounds of Examples 1, 4, 5, 9 and 11 which are shown below.

EXAMPLE 1

Preparation of N,N'-bis-[2,4-bis-[N-(1,2,2,6,6-pentamethyl-4-piperidyl)-butylamino]-1,3,5-triazin-6-yl]-1,6-hexanediamine a) 84.9 g (0.4 mol) of N-(2,2,6,6-tetramethyl-4-piperidyl)-butylamine are added slowly to a solution of 36.8 g (0.2 mol) of cyanuric chloride in 250 ml of xylene cooled to 10° C., maintaining the temperature between 10° and 15° C. After the end of the addition, the mixture is stirred for 1 hour at ambient temperature, and a solution of 16.8 g (0.42 mol) of sodium hydroxide in 70 ml of water is added.

The mixture is heated for 2 hours at 80° C., and 11.6 g (0.1 mol) of 1,6-hexanediamine and 12 g (0.3 mol) of sodium hydroxide are then added.

The mixture is then heated for 3 hours under total reflux and subsequently for a further 16 hours while separating off the water of reaction and, finally, 150 ml of water are added, the mixture is stirred for 10 minutes and the aqueous phase is separated off.

b) A mixture consisting of 19.8 g (0.43 mol) of formic acid and of a solution obtained by dissolving 13.5 g (0.44 mol) of paraformaldehyde in 24.5 ml of 2% aqueous NaOH solution is added in the course of about 2 hours to the solution obtained above and heated to 110° C., the water added and the water of reaction simultaneously being separated off azeotropically.

The mixture is then cooled to 70°–80° C. and a solution of 3 g of sodium hydroxide in 20 ml of water is added at 70°–80° C.

The aqueous layer is separated off and the mixture is dehydrated, separating off the water azeotropically.

The solution is then evaporated in vacuo (26 mbar), giving a product of melting point = 110°–114° C.

Analysis for $C_{68}H_{130}N_{16}$: Calculated: C = 69.70%; H = 11.18%; N = 19.12%. Found: C = 69.10%; H = 11.08%; N = 18.95%.

EXAMPLES 2–11

Following the procedure described in Example 1, under the same reaction conditions and using the appropriate reagents, the following compounds of the formula

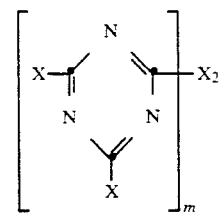

are prepared:

| Example | X | m | X₂ | Melting point (°C.) |
|---|---|---|---|---|
| 2 | (2,2,6,6-tetramethyl-1-n-butyl-4-piperidinyl)(methylamino) | 1 | (2,2,6,6-tetramethyl-1-n-butyl-4-piperidinyl)(methylamino) | 144–145 |
| 3 | CH₂=CH—CH₂—NH— | 2 | —N—(CH₂)₆—N— with 2,2,6,6-tetramethyl-1-methyl-4-piperidinyl groups | 147–150 |
| 4 | (2,2,6,6-tetramethyl-1-methyl-4-piperidinyl)(ethylamino) | 2 | —NH—(CH₂)₆—NH— | 118–120 |
| 5 | (2,2,6,6-tetramethyl-1-methyl-4-piperidinyl)(n-butylamino) | 2 | —NH—(CH₂)₂—N(piperazine)N— | 132–135 |
| 6 | (2,2,6,6-tetramethyl-1-methyl-4-piperidinyl)(methylamino) | 2 | —NH—(CH₂)₂—N(piperazine)N— | 175–178 |
| 7 | (2,2,6,6-tetramethyl-1-methyl-4-piperidinyl)(ethylamino) | 2 | —NH—(CH₂)₂—N(piperazine)N— | 172–177 |
| 8 | [(2,2,6,6-tetramethyl-1-methyl-4-piperidinyl)]₂N— | 2 | —NH—(CH₂)₂—N(piperazine)N— | 236–241 |

-continued

| Example | X | m | $X_2$ | Melting point (°C.) |
|---|---|---|---|---|
| 9 | H3C, CH3; H3C—N, H3C, CH3, CH3, C2H5, N— | 3 | $-NH-(CH_2)_2-N-(CH_2)_2-NH-$ | 220–222 |
| 10 | H3C, CH3; H3C—N, H3C, CH3, CH3, C2H5, N— | 3 | $-NH-(CH_2)_3-N-(CH_2)_3-NH-$ | 185–187 |
| 11 | H3C, CH3; H3C—N, H3C, CH3, CH3, n-C4H9, N— | 4 | $-NH-(CH_2)_3-N-(CH_2)_2-N-(CH_2)_3-NH-$ | 160–167 |

EXAMPLE 12

Following the procedure described in Example 1, under the same reaction conditions and using the appropriate reagents, the compound of the formula

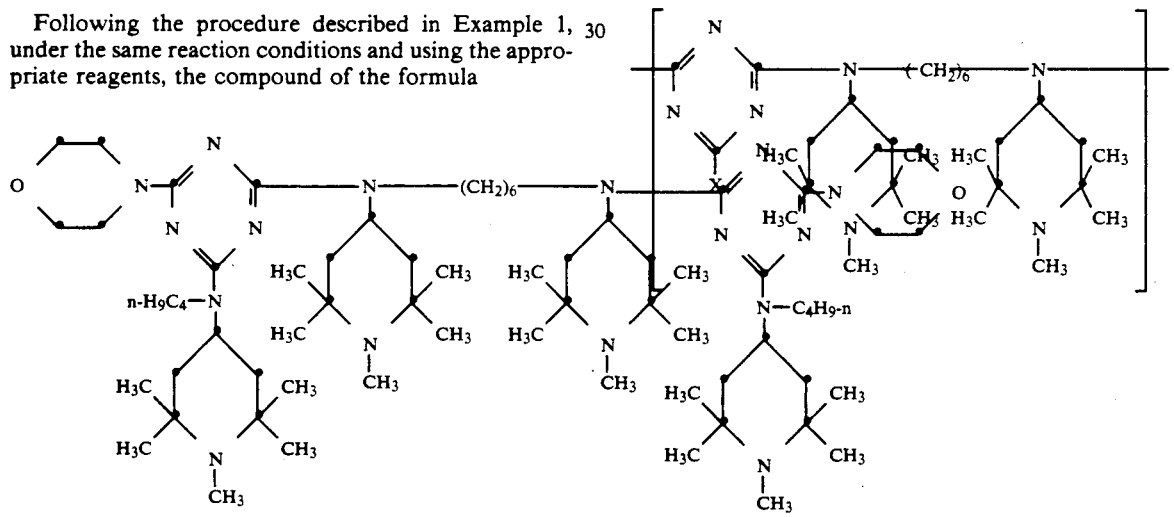

of melting point = 224°–226° C. is prepared.

EXAMPLES 13–14

Following the procedure described in Example 1, part b), under the same reaction conditions and using the appropriate intermediates, the following compounds containing the recurring unit of the formula are prepared:

| Example | $X_4$ | $\overline{M}n$ | Melting point (°C.) |
|---|---|---|---|
| 13 | $-NH-\underset{\underset{CH_3}{\mid}}{\overset{\overset{CH_3}{\mid}}{C}}-CH_2-\underset{\underset{CH_3}{\mid}}{\overset{\overset{CH_3}{\mid}}{C}}-CH_3$ | 2400 | 120–126 |

5,130,429

-continued

| Example | X₄ | $\overline{Mn}$ | Melting point (°C.) |
|---------|-----|-----|------|
| 14 | 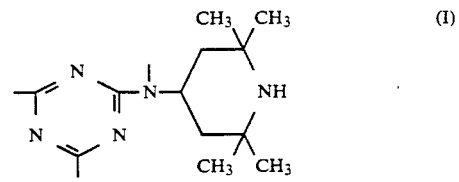 | 2150 | 163–168 |

The molecular weight is determined according to the method described in EP-A-255 990 on pages 18 and 19.

EXAMPLE 15

Preparation of N,N'-bis-[2,4-bis-[N-(1,2,2,6,6-pentamethyl-4-piperidyl)-butylamino]-1,3,5-triazin-6-yl]-N,N'-dimethyl-1,6-hexanediamine 17.4 g (0.378 mol) of formic acid and 12.97 g (0.432 mol) of paraformaldehyde suspended in 30 ml of water are added to a solution of 6.235 g (0.054 mol) of N,N'-bis-[2,4-bis-[N-(2,2,6,6-tetramethyl-4-piperidyl)-butylamino]-1,3,5-triazin-6-yl]-1,6-hexanediamine, prepared as described in Example 1a, in 90 ml of xylene.

The reaction vessel is closed and heated for 7 hours at 130° C. The mixture is then cooled, and a solution of 32 g (0.8 mol) of sodium hydroxide in 70 ml of water is added.

The mixture is heated for ½ hour at 80° C. with stirring.

The xylene solution is separated off, washed twice and evaporated in vacuo (2 mbar), giving a product, after drying in an oven, of melting point=111°–114° C.

Analysis for $C_{70}H_{134}N_{16}$: Calculated: C=70.07%; H=11.26%; N=18.68%. Found: C=69.94%; H=11.26%; N=18.62%.

EXAMPLE 16

Preparation of 2-chloro-4,6-bis[N-(1,2,2,6,6-pentamethyl-4-piperidyl)-butylamino]-1,3,5-triazine.

84.9 (0.4 mol) of N-(2,2,6,6-tetramethyl-4-piperidyl)-butylamine are slowly added to a solution of 36.8 g (0.2 mol) of cyanuric chloride in 250 ml of xylene cooled to 10° C., maintaining the temperature between 10° and 15° C. After the end of the addition, the mixture is stirred for 1 hour at room temperature and a solution of 16.8 g (0.42 mol) of sodium hydroxide in 70 ml of water is added.

The mixture is heated for 2 hours at 80° C., cooled to room temperature, the aqueous phase being separated off.

The organic phase is washed twice with water and then heated to 110° C. A mixture consisting of 21.2 g (0.46 mol) of formic acid and of a solution obtained by dissolving 15.3 g (0.50 mol) of paraformaldehyde in 27.8 ml of 2% aqueous NaOH solution is added in the course of about 2 hours to the organic solution obtained above and heated to 110° C., the added water and the water of reaction simultaneously being separated off azeotropically.

The mixture is then cooled to 70°–80° C. and a solution of 3.3 g of sodium hydroxide in 22 ml of water is added at 70°–80° C.

The aqueous layer is separated off and the mixture is dehydrated, separating off the water azeotropically.

The solution is then evaporated in vacuo (26 mbar), giving a product of m.p.=131°–133° C.

Analysis for $C_{31}H_{58}ClN_7$: Calculated: Cl=6.28%. Found: Cl=6.30%.

What is claimed is:

1. A process for the methylation of a compound containing at least one group of the formula (I)

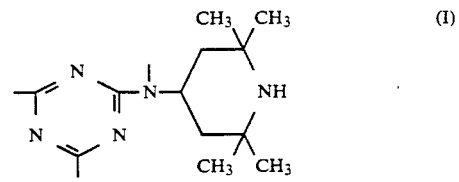

by means of a mixture of formaldehyde and formic acid to give the corresponding compound containing at least one group of the formula (II)

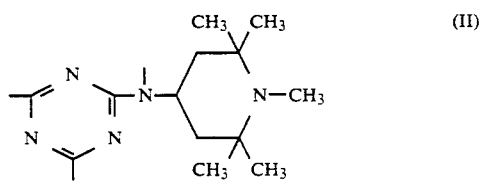

which comprises effecting said methylation in toluene, xylene or trimelhybenzene solvent wherein
  (1) the molar ratio of the NH groups in the piperidine of the formula (I), formaldehyde and formic acid is 1:1:1 to 1:2:2;
  (2) the water formed during the methylation reaction and that contained in the reagents is simultaneously removed from the reaction mixture by azeotropic distillation; and
  (3) the methylation reaction temperature is 80° C. to 150° C.

2. A process according to claim 1, wherein the aromatic hydrocarbon solvent is xylene.

3. A process according to claim 1, wherein the molar ratio of the >NH groups in the piperidine of the formula (I), formaldehyde and formic acid is 1:1:1 to 1:1.3:1.3.

4. A process according to claim 1, wherein the molar ratio of the >NH groups of the piperidine of the formula (I), formaldehyde and formic acid is 1:1:1 to 1:1.2:1.2.

5. A process according to claim 1, wherein the reaction temperature is 90° to 130° C.

6. A process according to claim 1, wherein the compound containing at least one group of the formula (II) is of the formula (III)

$$\left[ \begin{array}{c} X_1 \diagup\!\!\!\diagdown \diagup\!\!\!\diagdown\!\!-X_2 \\ N \quad N \\ \diagdown\!\!\diagup \\ X \end{array} \right]_m \quad (III)$$

in which X and $X_1$, which are identical or different, are one of the groups

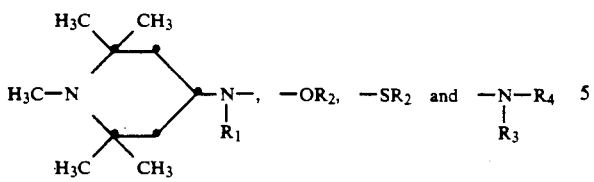
, $-OR_2$, $-SR_2$ and 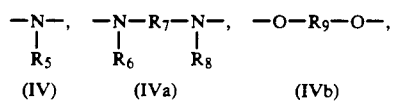

where $R_1$ is hydrogen, $C_1$-$C_{12}$alkyl, $C_5$-$C_7$cycloalkyl which is unsubstituted or substituted by $C_1$-$C_4$alkyl, $C_2$-$C_4$alkyl monosubstituted in the 2-, 3- or 4-position by OH, $C_1$-$C_8$alkoxy or $C_2$-$C_8$dialkylamino, benzyl or 1,2,2,6,6-pentamethyl-4-piperidyl, $R_2$ is $C_1$-$C_{12}$alkyl, $C_5$-$C_7$cycloalkyl which is unsubstituted or substituted by $C_1$-$C_4$alkyl, allyl, phenyl, benzyl or 1,2,2,6,6-pentamethyl-4-piperidyl and $R_3$ and $R_4$, which are identical or different, are hydrogen, $C_1$-$C_{12}$alkyl, $C_5$-$C_7$cycloalkyl which is unsubstituted or substituted by $C_1$-$C_4$alkyl, allyl, $C_2$-$C_4$alkyl monosubstituted in the 2-, 3- or 4-position by OH, $C_1$-$C_8$alkoxy or $C_2$-$C_8$dialkylamino, or benzyl, or $R_3$ and $R_4$, together with the nitrogen atom to which they are linked, form part of a 5-membered to 7-membered heterocyclic ring, m is an integer from 1 to 6 and, if m is 1, $X_2$ is as defined above for X and $X_1$ or is Cl or Br and, if m is 2, $X_2$ is one of the groups of the formulae (IV)-(IVe)

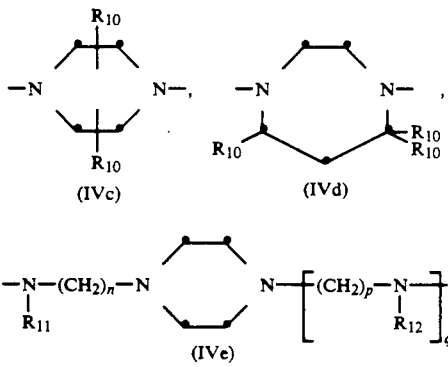

in which $R_5$ is as defined above for $R_1$, and $R_6$, $R_8$, $R_{11}$ and $R_{12}$, which are identical or different, are hydrogen, $C_1$-$C_{12}$alkyl, $C_5$-$C_7$cycloalkyl which is unsubstituted or substituted by $C_1$-$C_4$alkyl or are benzyl or 1,2,2,6,6-pentamethyl-4-piperidyl, $R_7$ is $C_2$-$C_{12}$alkylene, $C_5$-$C_{18}$cycloalkylene, $C_8$-$C_{18}$dialkylenecyclohexylene, $C_{13}$-$C_{18}$alkylenedicyclohexylene, $C_{14}$-$C_{18}$alkylidenedicyclohexylene, xylylene, $C_4$-$C_{12}$alkylene which is interrupted by one, two or three oxygen atoms or $>N$—$R_{13}$ groups, $R_{13}$ being $C_1$-$C_{12}$alkyl or cyclohexyl, $R_9$ is $C_2$-$C_{12}$alkylene, $C_5$-$C_{18}$cycloalkylene, $C_8$-$C_{18}$dialkylenecyclohexylene, $C_{13}$-$C_{18}$alkylenedicyclohexylene, $C_{14}$-$C_{18}$alkylidenedicyclohexylene, phenylene, $C_{13}$-$C_{26}$alkylenediphenylene or $C_{14}$-$C_{26}$alkylidenediphenylene which is unsubstituted or substituted on the benzene ring by $C_1$-$C_4$alkyl, $R_{10}$ is hydrogen or methyl, n and p, which are identical or different, are integers from 2 to 6 and q is zero or 1, and, if m is 3, $X_2$ is one of the groups

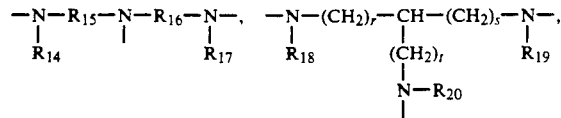

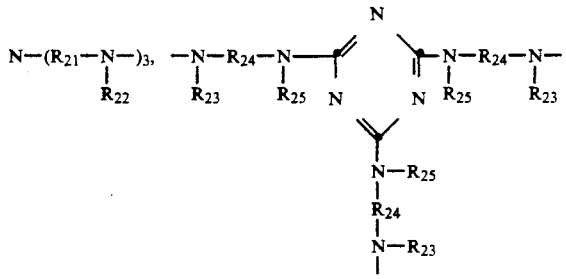

in which $R_{14}$, $R_{17}$, $R_{18}$, $R_{19}$, $R_{20}$, $R_{22}$, $R_{23}$ and $R_{25}$, which are identical or different, are as defined for $R_6$ and $R_8$, and $R_{15}$, $R_{16}$, $R_{21}$ and $R_{24}$, which are identical or different, are $C_2$-$C_{12}$alkylene, or $R_{15}$ and $R_{16}$ are $C_4$-$C_6$alkylene which is interrupted by an $>N$—$CH_3$ group, r and s, which are identical or different, are integers from 2 to 6 and t is zero or 1, and, if m is 4, 5 or 6, $X_2$ is a group

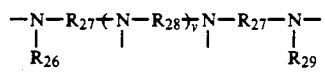

where $R_{26}$ and $R_{29}$, which are identical or different, are as defined for $R_6$ and $R_8$, and $R_{27}$ and $R_{28}$, which are identical or different, are $C_2$-$C_{12}$-alkylene and v is 1, 2 or 3, or, if m is 4, $X_2$ is additionally one of the groups

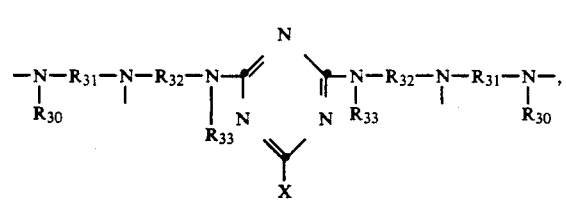

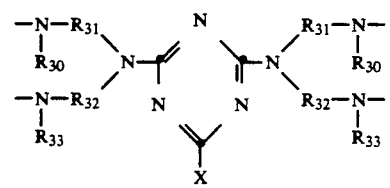

where $R_{30}$ and $R_{33}$, which are identical or different, are as defined above for $R_6$ and $R_8$, and $R_{31}$ and $R_{32}$, which are identical or different, are $C_2$-$C_{12}$alkylene and X is as defined above, or, if m is 6, $X_2$ is additionally one of the groups

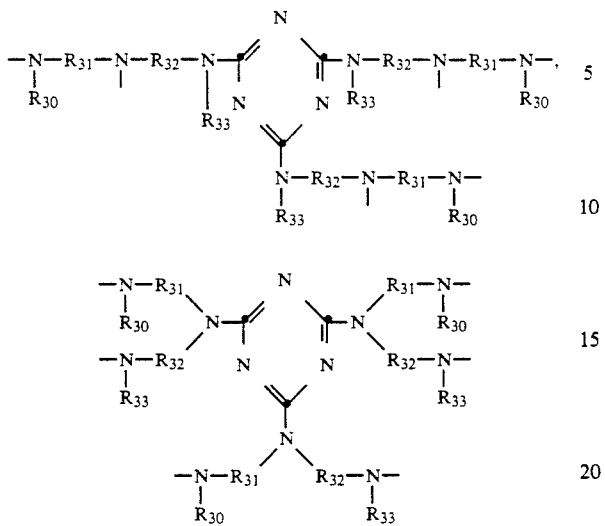

where $R_{30}$, $R_{31}$, $R_{32}$ and $R_{33}$ are as defined above, with the proviso that, in this compound of the formula (III), at least one 1,2,2,6,6-pentamethyl-4-piperidyl group is present in at least one of the groups X, $X_1$ and $X_2$.

7. A process according to claim 1, wherein the compound containing at least one group of the formula (II) is of the formula (V)

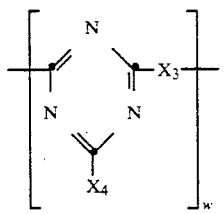

(V)

in which $X_3$ is one of the groups of the formulae (IVa), (IVb), (IVc), (IVd) and (IVe)

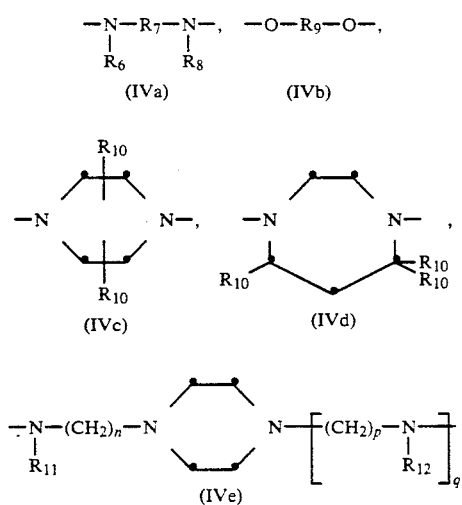

or a group of the formula

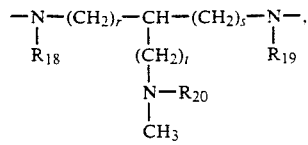

$R_6$, $R_8$, $R_{11}$, $R_{18}$, $R_{19}$ and $R_{20}$, which are identical or different, are hydrogen, $C_1$-$C_{12}$alkyl, $C_5$-$C_7$cycloalkyl which is unsubstituted or substituted by $C_1$-$C_4$alkyl or are benzyl or 1,2,2,6,6-pentamethyl-4-piperidyl, $R_7$ is $C_2$-$C_{12}$alkylene, $C_5$-$C_{18}$cycloalkylene, $C_8$-$C_{18}$dialkylenecyclohexylene, $C_{13}$-$C_{18}$alkylenedicyclohexylene, $C_{14}$-$C_{18}$alkylidenedicyclohexylene, xylylene, $C_4$-$C_{12}$alkylene which is interrupted by one, two or three oxygen atoms or >N—$R_{13}$ groups, $R_{13}$ being $C_1$-$C_{12}$alkyl or cyclohexyl, $R_9$ is $C_2$-$C_{12}$alkylene, $C_5$-$C_{18}$cycloalkylene, $C_8$-$C_{18}$dialkylenecyclohexylene, $C_{13}$-$C_{18}$alkylenedicyclohexylene, $C_{14}$-$C_{18}$alkylidenedicyclohexylene, phenylene, $C_{13}$-$C_{26}$alkylenediphenylene or $C_{14}$-$C_{26}$alkylidenediphenylene which is unsubstituted or substituted on the benzene ring by $C_1$-$C_4$alkyl, $R_{10}$ is hydrogen or methyl, n, p, r and s, which are identical or different, are integers from 2 to 6 and q and t are zero or 1, $X_4$ is one of the groups

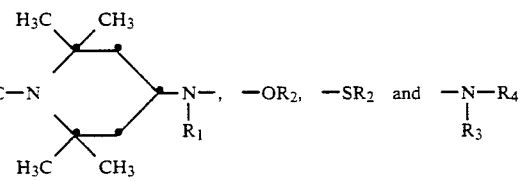

where $R_1$ is hydrogen, $C_1$-$C_{12}$alkyl, $C_5$-$C_7$cycloalkyl which is unsubstituted or substituted by $C_1$-$C_4$alkyl, $C_2$-$C_4$alkyl monosubstituted in the 2-, 3- or 4-position by OH, $C_1$-$C_8$alkoxy or $C_2$-$C_8$dialkylamino, benzyl or 1,2,2,6,6-pentamethyl-4-piperidyl, $R_2$ is $C_1$-$C_{12}$alkyl, $C_5$-$C_7$cycloalkyl which is unsubstituted or substituted by $C_1$-$C_4$alkyl, allyl, phenyl, benzyl or 1,2,2,6,6-pentamethyl-4-piperidyl and $R_3$ and $R_4$, which are identical or different, are hydrogen, $C_1$-$C_{12}$alkyl, $C_5$-$C_7$cycloalkyl which is unsubstituted or substituted by $C_1$-$C_4$alkyl, allyl, $C_2$-$C_4$alkyl monosubstituted in the 2-, 3- or 4-position by OH, $C_1$-$C_8$alkoxy or $C_2$-$C_8$dialkylamino, or benzyl, or $R_3$ and $R_4$, together with the nitrogen atom to which they are linked, form part of a 5-membered to 7-membered heterocyclic ring, and w is a number from 2 to 50, with the proviso that, in this compound of the formula (V) at least one 1,2,2,6,6-pentamethyl-4-piperidyl group is present in at least one of the groups $X_3$ and $X_4$.

8. A process according to claim 1, wherein the compound containing at least one group of the formula (II) is a compound containing recurring units of the formulae (VI) and (VII)

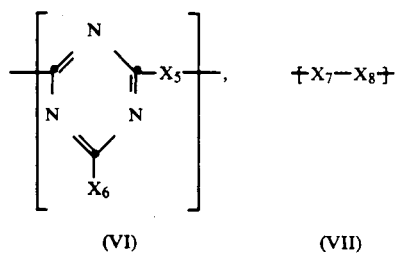

and having a molecular weight between 1000 and 20,000, in which the (VI):(VII) molar ratio is 4:1 to 1:4, $X_5$ and $X_8$, which are identical or different, are one of the groups of the formulae (IVa), (IVb), (IVc), (IVd) and (IVe)

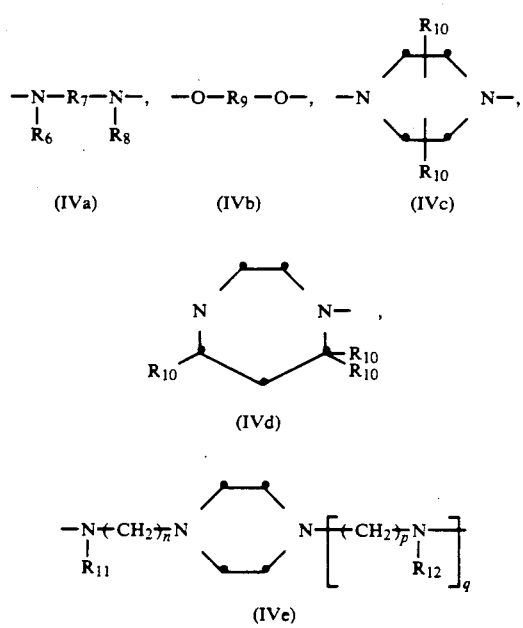

or a group of the formula

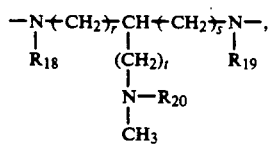

$R_6$, $R_8$, $R_{11}$, $R_{12}$, $R_{18}$, $R_{19}$ and $R_{20}$, which are identical or different, are hydrogen, $C_1$-$C_{12}$alkyl, $C_5$-$C_7$cycloalkyl which is unsubstituted or substituted by $C_1$-$C_4$alkyl or are benzyl or 1,2,2,6,6-pentamethyl-4-piperidyl, $R_7$ is $C_2$-$C_{12}$alkylene, $C_5$-$C_{18}$cycloalkylene, $C_8$-$C_{18}$dialkylenecyclohexylene, $C_{13}$-$C_{18}$alkylenedicyclohexylene, $C_{14}$-$C_{18}$alkylidenedicyclohexylene, xylylene, $C_4$-$C_{12}$alkylene which is interrupted by one, two or three oxygen atoms or >N—$R_{13}$ groups, $R_{13}$ being $C_1$-$C_{12}$alkyl or cyclohexyl, $R_9$ is $C_2$-$C_{12}$alkylene, $C_5$-$C_{18}$cycloalkylene, $C_8$-$C_{18}$dialkylenecyclohexylene, $C_{13}$-$C_{18}$alkylenedicyclohexylene, $C_{14}$-$C_{18}$alkylidenedicyclohexylene, phenylene, $C_{13}$-$C_{26}$alkylenediphenylene or $C_{14}$-$C_{26}$alkylidenediphenylene which is unsubstituted or substituted on the benzene ring by $C_1$-$C_4$alkyl, $R_{10}$ is hydrogen or methyl, n, p, r and s, which are identical or different, are integers from 2 to 6 and q and t are zero or 1, $X_6$ is one of the groups

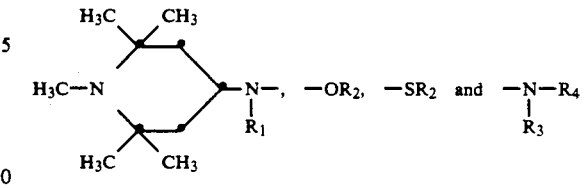

where $R_1$ is hydrogen, $C_1$-$C_{12}$alkyl, $C_5$-$C_7$cycloalkyl which is unsubstituted or substituted by $C_1$-$C_4$alkyl, $C_2$-$C_4$alkyl monosubstituted in the 2-, 3- or 4-position by OH, $C_1$-$C_8$alkoxy or $C_2$-$C_8$dialkylamino, benzyl or 1,2,2,6,6-pentamethyl-4-piperidyl, $R_2$ is $C_1$-$C_{12}$alkyl, $C_5$-$C_7$cycloalkyl which is unsubstituted or substituted by $C_1$-$C_4$alkyl, allyl, phenyl, benzyl or 1,2,2,6,6-pentamethyl-4-piperidyl and $R_3$ and $R_4$, which are identical or different, are hydrogen, $C_1$-$C_{12}$alkyl, $C_5$-$C_7$cycloalkyl which is unsubstituted or substituted by $C_1$-$C_4$alkyl, allyl, $C_2$-$C_4$alkyl monosubstituted in the 2-, 3- or 4-position by OH, $C_1$-$C_8$alkoxy or $C_2$-$C_8$dialkylamino, or benzyl, or $R_3$ and $R_4$, together with the nitrogen atom to which they are linked, form part of a 5-membered to 7-membered heterocyclic ring, $X_7$ is $C_2$-$C_{12}$alkylene, a group

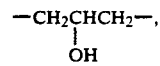

aliphatic $C_2$-$C_{12}$diacyl, —$CH_2CO$—, a group —COO—$R_9$—OOC— with $R_9$ as defined above, or $X_7$ is a group

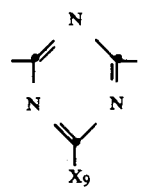

with $X_9$ as defined above for $X_6$, with the proviso that, in this compound, at least one 1,2,2,6,6-pentamethyl-4-piperidyl group is present in at least one of the radicals $X_5$, $X_6$ and $X_8$.

9. A process according to claim 1, wherein the compound containing at least one group of the formula (II) is of the formula (VIII)

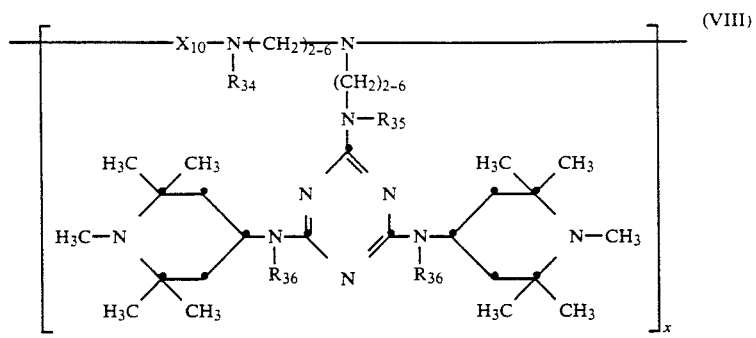
(VIII)

in which $X_{10}$ is $C_2$-$C_{12}$alkylene, a group

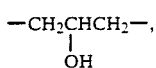

aliphatic $C_2$-$C_{12}$diacyl, —$CH_2CO$—, a group —COO—$R_9$—OOC— with $R_9$ being $C_2$-$C_{12}$alkylene, $C_5$-$C_{18}$cycloalkylene, $C_8$-$C_{18}$dialkylenecyclohexylene, $C_{13}$-$C_{18}$alkylenedicyclohexylene, $C_{14}$-$C_{18}$alkylidenedicyclohexylene, phenylene, $C_{13}$-$C_{26}$-alkylenediphenylene or $C_{14}$-$C_{26}$alkylidenediphenylene which is unsubstituted or substituted on the benzene ring by $C_1$-$C_4$alkyl, or $X_{10}$ is a group

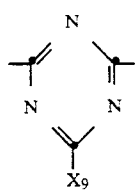

where $X_9$ is one of the groups

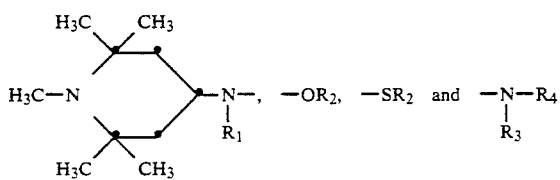

where $R_1$ is hydrogen, $C_1$-$C_{12}$alkyl, $C_5$-$C_7$cycloalkyl which is unsubstituted or substituted by $C_1$-$C_4$alkyl, $C_2$-$C_4$alkyl monosubstituted in the 2-, 3- or 4-position by OH, $C_1$-$C_8$alkoxy or $C_2$-$C_8$dialkylamino, benzyl or 1,2,2,6,6-pentamethyl-4-piperidyl, $R_2$ is $C_1$-$C_{12}$alkyl, $C_5$-$C_7$cycloalkyl which is unsubstituted or substituted by $C_1$-$C_4$alkyl, allyl, phenyl, benzyl or 1,2,2,6,6-pentamethyl-4-piperidyl and $R_3$ and $R_4$, which are identical or different, are hydrogen, $C_1$-$C_{12}$alkyl, $C_5$-$C_7$cycloalkyl which is unsubstituted or substituted by $C_1$-$C_4$alkyl, allyl, $C_2$-$C_4$alkyl monosubstituted in the 2-, 3- or 4-position by OH, $C_1$-$C_8$alkoxy or $C_2$-$C_8$dialkylamino, or benzyl, or $R_3$ and $R_4$, together with the nitrogen atom to which they are linked, form part of a 5-membered to 7-membered heterocyclic ring, $R_{34}$ and $R_{35}$, which are identical or different, are hydrogen or $C_1$-$C_{12}$alkyl or $R_{34}$ is additionally a group of the formula (IX)

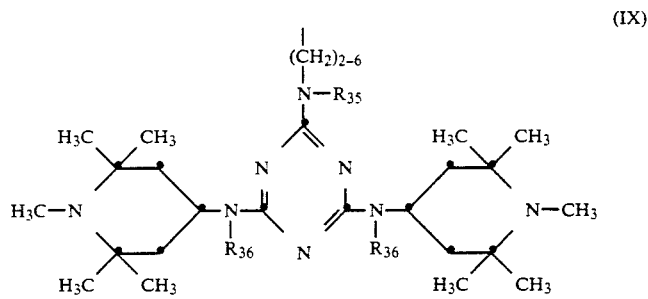
(IX)

with $R_{35}$ as defined above, $R_{36}$ is hydrogen, $C_1$-$C_{12}$alkyl, cyclohexyl or benzyl, and x is a number from 2 to 50.

10. A process according to claim 1, wherein the compound containing at least one group of the formula (II) is of the formula (IIIa)

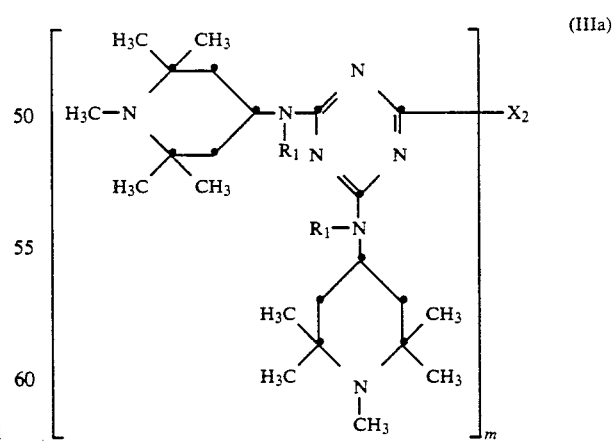
(IIIa)

in which $R_1$ is $C_1$-$C_8$alkyl, cyclohexyl, 1,2,2,6,6-pentamethyl-4-piperidyl or $C_2$-$C_3$alkyl monosubstituted in the 2- or 3-position by OH, $C_1$-$C_4$alkoxy or $C_2$-$C_4$dialkylamino, m is an integer from 1 to 4, and, if m is 1, $X_2$ is Cl or one of the groups

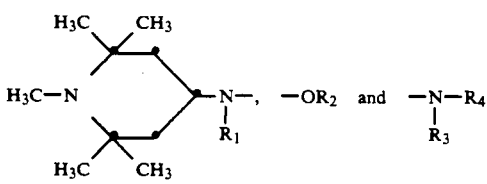

where R₁ is as defined above, R₂ is $C_1$-$C_8$alkyl or 1,2,2,6,6-pentamethyl-4-piperidyl and R₃ and R₄, which are identical or different, are hydrogen, $C_1$-$C_8$alkyl, cyclohexyl or allyl or

represents 4-morpholinyl, and, if m is 2, X₂ is one of the groups

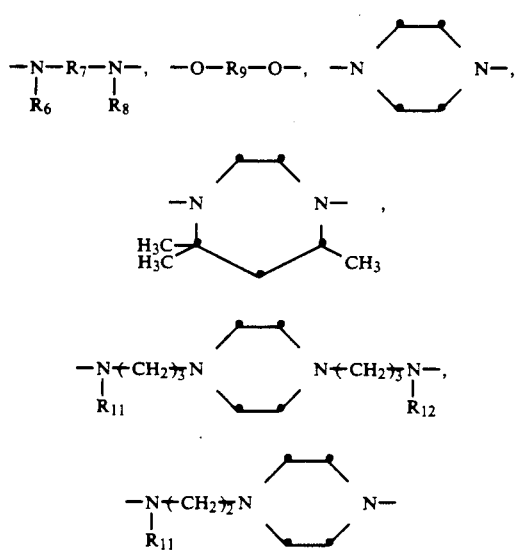

where R₆, R₈, R₁₁ and R₁₂, which are identical or different, are hydrogen, $C_1$-$C_4$alkyl, cyclohexyl or 1,2,2,6,6-pentamethyl-4-piperidyl, R₇ is $C_2$-$C_6$alkylene, cyclohexylene, cyclohexylenedimethylene, methylenedicyclohexylene or $C_4$-$C_{12}$alkylene which is interrupted by one or two oxygen atoms or >N—CH₃ groups and R₉ is $C_2$-$C_6$alkylene, cyclohexylene, cyclohexylenedimethylene, isopropylidenedicyclohexylene, phenylene, methylenediphenylene or isopropylidenediphenylene, and, if m is 3, X₂ is a group

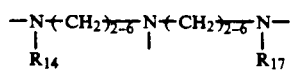

where R₁₄ and R₁₇, which are identical or different, are hydrogen, $C_1$-$C_4$alkyl or 1,2,2,6,6-pentamethyl-4-piperidyl, and, if m is 4, X₂ is a group

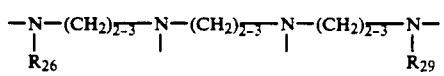

where R₂₆ and R₂₉, which are identical or different, are hydrogen, $C_1$-$C_4$alkyl or 1,2,2,6,6-pentamethyl-4-piperidyl.

11. A process according to claim 1, wherein the compound containing at least one group of the formula (II) is of the formula (Va)

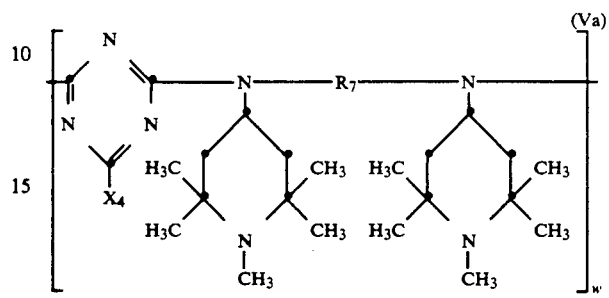

in which R₇ is $C_2$-$C_6$alkylene, cyclohexylene, cyclohexylenedimethylene, methylenedicyclohexylene or $C_4$-$C_{12}$alkylene which is interrupted by one or two oxygen atoms or >N—CH₃ groups, X₄ is one of the groups

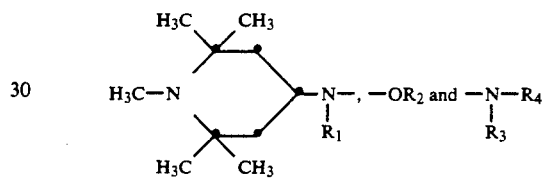

where R₁ is $C_1$-$C_8$alkyl, cyclohexyl, 1,2,2,6,6-pentamethyl-4-piperidyl or $C_2$-$C_3$alkyl monosubstituted in the 2- or 3-position by OH, $C_1$-$C_4$alkoxy or $C_2$-$C_4$dialkylamino, R₂ is $C_1$-$C_8$alkyl or 1,2,2,6,6-pentamethyl-4-piperidyl, R₃ and R₄, which are identical or different, are hydrogen, $C_1$-$C_8$alkyl, cyclohexyl or allyl, or

is 4-morpholinyl and w is a number from 2 to 20.

12. A process according to claim 8, wherein the compound containing at least one group of the formula (II) is a compound containing recurring units of the formulae (VI) and (VII), and having a molecular weight between 1500 and 10,000 and a (VI):(VII) molar ratio of 3:1 to 1:3, in which X₅ and X₈ are groups of the formula

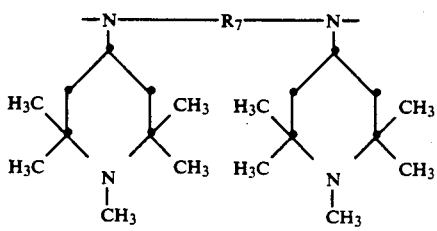

where R₇ is $C_2$-$C_6$alkylene, cyclohexylene, cyclohexylenedimethylene, methylenedicyclohexylene or $C_4$-$C_{12}$alkylene which is interrupted by one or two oxygen atoms or >N—CH₃ groups, X₆ is one of the groups

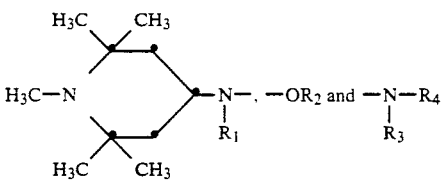

where $R_1$ is $C_1$-$C_8$alkyl, cyclohexyl, 1,2,2,6,6-pentamethyl-4-piperidyl or $C_2$-$C_3$alkyl monosubstituted in the 2- or 3-position by OH, $C_1$-$C_4$alkoxy or $C_2$-$C_4$dialkylamino, $R_2$ is $C_1$-$C_8$alkyl or 1,2,2,6,6-pentamethyl-4-piperidyl and $R_3$ and $R_4$, which are identical or different, are hydrogen, $C_1$-$C_8$-alkyl, cyclohexyl or allyl, or

is 4-morpholinyl and $X_7$ is

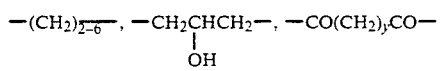

with y being zero to 8, or a —CH₂CO— group.

13. A process according to claim 9, wherein the compound containing at least one group of the formula (II) is of the formula (VIII) in which $X_{10}$ is

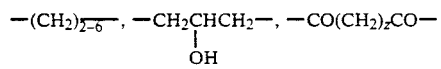

with z being zero to 8, a —CH₂CO— group or a group

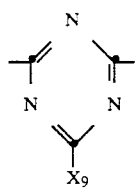

where $X_9$ is one of the groups

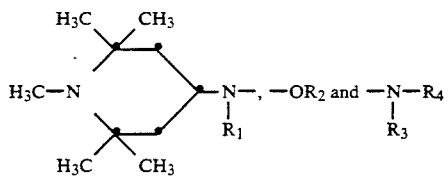

in which $R_1$ is $C_1$-$C_8$alkyl, cyclohexyl or 1,2,2,6,6-pentamethyl-4-piperidyl, $R_2$ is $C_1$-$C_8$alkyl or 1,2,2,6,6-pentamethyl-4-piperidyl, and $R_3$ and $R_4$, which are identical or different, are hydrogen, $C_1$-$C_8$alkyl, cyclohexyl or allyl, or

is 4-morpholinyl, $R_{34}$ and $R_{35}$, which are identical or different, are hydrogen or methyl, or $R_{34}$ is a group of the formula (IX) with $R_{35}$ being hydrogen or methyl, $R_{36}$ is $C_1$-$C_8$alkyl or cyclohexyl and x is a number from 2 to 20.

14. A process according to claim 10, wherein the compound containing at least one group of the formula (II) is of the formula (IIIa) in which $R_1$ is $C_1$-$C_8$alkyl, cyclohexyl or 1,2,2,6,6-pentamethyl-4-piperidyl, m is an integer from 1 to 4, and, if m is 1, $X_2$ is Cl or one of the groups

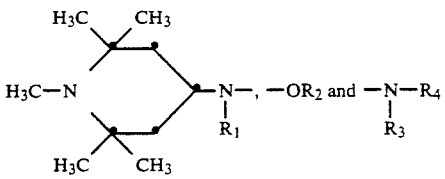

where $R_1$ is as defined above, $R_2$ is $C_1$-$C_8$alkyl or 1,2,2,6,6-pentamethyl-4-piperidyl, and $R_3$ and $R_4$, which are identical or different, are $C_1$-$C_8$alkyl, cyclohexyl or allyl, and $R_3$ is additionally hydrogen, or

is 4-morpholinyl, and, if m is 2, $X_2$ is one of the groups

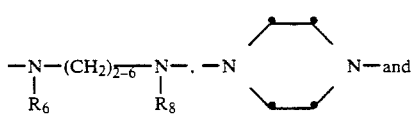

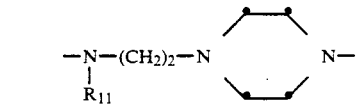

where $R_6$, $R_8$ and $R_{11}$, which are identical or different, are hydrogen, methyl or 1,2,2,6,6-pentamethyl-4-piperidyl, and, if m is 3, $X_2$ is a group

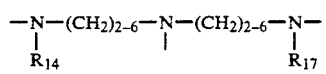

where $R_{14}$ and $R_{17}$, which are identical or different, are hydrogen, methyl or 1,2,2,6,6-pentamethyl-4-piperidyl, and, if m is 4, $X_2$ is a group

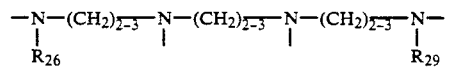

where $R_{26}$ and $R_{29}$, which are identical or different, are hydrogen or methyl.

15. A process according to claim 11, wherein the compound containing at least one group of the formula (II) is of the formula (Va) in which $R_7$ is —(CH₂)₂₋₆—, $X_4$ is one of the groups

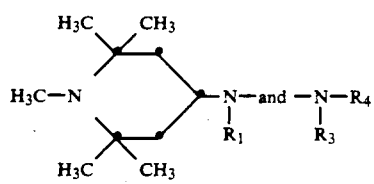 and 
where $R_1$ is $C_1$-$C_8$alkyl, cyclohexyl or 1,2,2,6,6-pentamethyl-4-piperidyl, $R_3$ and $R_4$, which are identical or different, are $C_1$-$C_8$alkyl or cyclohexyl, and $R_3$ is additionally hydrogen, or
$$-\underset{R_3}{\underset{|}{N}}-R_4$$
is 4-morpholinyl, and w is a number from 2 to 10.
* * * * *